(12) United States Patent
Phadke et al.

(10) Patent No.: US 11,759,446 B2
(45) Date of Patent: Sep. 19, 2023

(54) LIQUID TASIMELTEON FORMULATIONS AND METHODS OF USE THEREOF

(71) Applicant: Vanda Pharmaceuticals Inc., Washington, DC (US)

(72) Inventors: Deepak Phadke, Olathe, KS (US); Mihael Polymeropoulos, Potomac, MD (US)

(73) Assignee: VANDA PHARMACEUTICALS INC., Washington, DC (US)

( * ) Notice: Subject to any disclaimer, the term of this patent is extended or adjusted under 35 U.S.C. 154(b) by 72 days.

(21) Appl. No.: 17/216,427

(22) Filed: Mar. 29, 2021

(65) Prior Publication Data
US 2021/0212980 A1 Jul. 15, 2021

Related U.S. Application Data

(62) Division of application No. 17/119,953, filed on Dec. 11, 2020, now Pat. No. 11,202,770.

(60) Provisional application No. 62/947,774, filed on Dec. 13, 2019, provisional application No. 62/972,902, filed on Feb. 11, 2020, provisional application No. 63/119,488, filed on Nov. 30, 2020.

(51) Int. Cl.
| | |
|---|---|
| *A61K 31/343* | (2006.01) |
| *A61K 47/02* | (2006.01) |
| *A61K 47/10* | (2017.01) |
| *A61K 47/26* | (2006.01) |
| *A61K 47/38* | (2006.01) |
| *A61K 9/08* | (2006.01) |

(52) U.S. Cl.
CPC ............ *A61K 31/343* (2013.01); *A61K 9/08* (2013.01); *A61K 47/02* (2013.01); *A61K 47/10* (2013.01); *A61K 47/26* (2013.01); *A61K 47/38* (2013.01)

(58) Field of Classification Search
CPC ...... A61K 31/343; A61K 47/02; A61K 47/10; A61K 47/26; A61K 47/32; A61K 47/36; A61K 47/38; A61K 9/0095; A61K 9/08; A61K 9/10
See application file for complete search history.

(56) References Cited

U.S. PATENT DOCUMENTS

| | | | |
|---|---|---|---|
| 5,856,529 A | 1/1999 | Catt et al. | |
| 10,179,119 B2 | 1/2019 | Lavedan et al. | |
| 10,653,665 B2 | 5/2020 | Lavedan et al. | |
| 2005/0137247 A1 | 6/2005 | Czeisler et al. | |
| 2008/0260837 A1 | 10/2008 | Namburi et al. | |
| 2009/0105333 A1* | 4/2009 | Birznieks | A61K 31/405 |
| | | | 514/469 |
| 2012/0136050 A1 | 5/2012 | Polymeropoulos et al. | |
| 2013/0197076 A1 | 8/2013 | Dressman et al. | |
| 2017/0355688 A1 | 12/2017 | Zhao | |

FOREIGN PATENT DOCUMENTS

| | | |
|---|---|---|
| CN | 102675268 A | 9/2012 |
| CN | 106542973 A | 3/2017 |
| WO | 2015108728 A1 | 7/2015 |
| WO | 2016036619 A1 | 3/2016 |

OTHER PUBLICATIONS

Sanchez-Barcelo et al., "Clinical Uses of Melatonin: Evaluation of Human Trials," Current Medicinal Chemistry, vol. 17, No. 19, pp. 2070-2095, 2010.
Tasimelteon, Case Analysis, FDA, 24, Nov. 12, 2013, vol. 11, No. 8, p. 44.
Chinese Office Action for Application No. 201580046852.7, dated Mar. 13, 2020 and English translation thereof, 7 pages.
Chinese Search Report for Application No. 201580046852.7, dated Mar. 13, 2020 and English translation thereof, 4 pages.
A. Van Thillo, et al. "Sleep Disturbances in Smith-Magenis syndrome: treatment with melatonin and beta-adrenergic antagonists," (Dutch translation with English Summary), Tijdschrift Voor Psychiatrie, 2010, vol. 52, No. 10, 719-723.
Hardeland, "New approaches in the management of insomnia: weighing the advantages of prolonged-release melatonin and synthetic melatoninergic agonists," Neuropsychiatric Disease and Treatment, Jan. 1, 2009, 341-354.
Anonymous, "Vanda Pharmaceuticals Management Discusses Q2 2013 Results," Jul. 31, 2013, retrieved from: http://www.nasdaq.com.aspx/call-transcript.aspx?StoryId=1591662&Title=vanda-pharmaceuticals-management-discusses-q2-2013-results-earnings-call-transcript on Oct. 14, 2015, 2 pages.
International Search Report and Written Opinion for PCT Application No. PCT/US2015/047610 dated Aug. 29, 2015, 16 pages.
Chinese Office Action for Chinese Application No. 201580046852.7, dated Feb. 28, 2019, 5 pages.
Leersnyder, "Inverted rhythm of melatonin secretion in Smith-Magenis syndrome: from symptoms to treatment," Trends Endocrinology and Metabolism, ScienceDirect, 2006, vol. 17, No. 7 pp. 291-298.
Bonacci et al., Tasimelteon (Hetlioz): A New Melatonin Receptor Agonist for the Treatment of N0n-24-Hour Sleep-Wake Disorder, Journal of Pharmacy Practice, 2015, vol. 28, No. 5, pp. 473-478, ePub: Aug. 3, 2014.
Clinical Diagnosis and Treatment of Neurology in Traditional Chinese Medicine, Peixin Huang et al., People's Medical Publishing House, Oct. 31, 2013, 480-482.
Decision of Rejection issued by the China National Intellectual Property Administration for Application No. 201580046852.7, dated Jan. 20, 2021, 9 pages.
Arendt et al., "Melatonin and its agonists: an update," The British Journal of Psychiatry (2008), Cambridge, vol. 193, pp. 267-269.
Rajaratnam et al., "Melatonin agonist tasimelteon (VEC-162) for transient insomnia after sleep-time shift: two randomised controlled multicentre trials", The Lancet 2009; vol. 373., pp. 482-491.
Vachharajani et al., "Preclinical Pharmacokinetics and Metabolism of BMS-214778, a Novel Melatonin Receptor Agonist", Journal of Pharmaceutical Sciences, Apr. 2003, vol. 92, No. 4, pp. 760-772.

(Continued)

*Primary Examiner* — Sarah Pihonak
(74) *Attorney, Agent, or Firm* — Hoffman Warnick LLC

(57) ABSTRACT

Liquid suspensions of tasimelteon and methods for their use.

14 Claims, 2 Drawing Sheets

(56) References Cited

OTHER PUBLICATIONS

Anonymous, "Hetlioz Approved for Nighttime Sleep Disturbances in Smith-Magenis Syndrome," Dec. 3, 2020, https://www.empr.com/home/news/hetlioz-tasimelteon-melatonin-smith-magenis-syndrome-sleep-disturbances.

Kulshreshtha A. et al., (ed.) "Pharmaceutical Suspensions—From Formulation Development to Manufacturing." Springer, Dec. 31, 2010, chapters 1, 2, 3 and 5.

Zhao, G.H. et al. "Characterisation of the interactive properties of microcrystalline cellulose-carboxymethyl cellulose hydrogels." International Journal of Pharmaceutics, vol. 30, No. 415, p. 95-101, May 27, 2011.

\* cited by examiner

A

B

C

D

E

F

LIQUID TASIMELTEON FORMULATIONS AND METHODS OF USE THEREOF

CROSS-REFERENCE TO RELATED APPLICATIONS

This application is a divisional application of co-pending U.S. patent application Ser. No. 17/119,953, filed 11 Dec. 2020, which claims priority to U.S. Provisional Patent Application Ser. Nos. 62/947,774, filed 13 Dec. 2019, 62/972,902, filed 11 Feb. 2020, and 63/119,488, filed 30 Nov. 2020, each of which is hereby incorporated in its entirety as though fully set forth.

BACKGROUND OF THE INVENTION

The present invention provides pharmaceutically elegant formulations comprising liquid suspensions of tasimelteon (see U.S. Pat. No. 5,856,529, claim 7) or trans-N-[[2-(2,3-dihydrobenzofuran-4-yl)cycloprop-1-yl]methyl]propanamide, which is the active ingredient in HETLIOZ©, a medicine approved for use in Non-24-Hour Sleep-Wake Disorder (Non-24) and is commercially available as a solid oral dosage form, i.e., capsules containing 20 mg of tasimelteon.

Preparing a pharmaceutically elegant suspension of a medicine that is suitable for administration to patients, particularly as a liquid formulation, presents an array of challenges, typical of which can be physical stability, content uniformity, sedimentation, caking, resuspendability, crystal growth, and undesirable taste or odor. See Alok K. Kulshreshtha, Onkar N. Singh, and G. Michael Wall (Eds.), "Pharmaceutical Suspensions: From Formulation Development to Manufacturing." Preparing a pharmaceutically elegant liquid suspension of tasimelteon suitable for administration to a patient, particularly pediatric patients, is particularly complicated by factors such as the unpalatable taste of tasimelteon, the necessity for achieving a viscosity suitable for measuring and administering an effective unit dose in a suitable volume of liquid, the chemical stability of liquid tasimelteon formulations, its dissolution rate and solubility in a liquid vehicle, and the opacity of the liquid formulations prepared as tasimelteon suspensions. Achieving a pharmaceutically elegant formulation of tasimelteon requires addressing in a successful manner each of such complicating factors, while at the same time assuring that the resulting formulation is readily manufacturable.

Heretofore, U.S. Pat. No. 5,856,529 (e.g., column 17) reported that pharmaceutical compositions of medicines, such as tasimelteon, could be prepared in formulations suitable for oral administration, including compositions with a liquid carrier used for preparing a syrup or an aqueous liquid suspension in which conventional additives such as suspending agents, emulsifying agents, wetting agents, and preservatives, as well as flavoring and/or coloring agents, could be used.

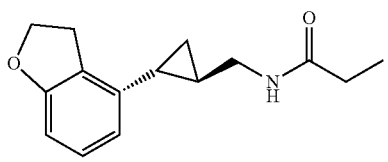

Tasimelteon

As is otherwise known in the art, tasimelteon can be prepared as a white to off-white powder with a melting point of about 78° C. (DSC). It is highly soluble in 95% ethanol, methanol, acetonitrile, ethyl acetate, isopropanol, polyethylene glycols (PEG-300 and PEG-400), but poorly soluble in water. The native pH of a saturated solution of tasimelteon in water is 8.5 and its aqueous solubility is substantially unaffected by pH.

SUMMARY OF THE INVENTION

The invention disclosed herein provides pharmaceutically elegant liquid compositions comprising tasimelteon in an aqueous suspension in which a predetermined volume of the pharmaceutical composition (e.g., 0.35-10 mL) will provide a unit dose of the active ingredient suspended therein, such that one or more such unit doses administered to an individual will provide an amount of tasimelteon that is effective to treat or prevent the disease or condition for which the medicine is being administered.

The pharmaceutical compositions of the present invention provide a homogeneous aqueous suspension of tasimelteon that may include one or more suspending agents and one or more taste masking agents. As an example, such compositions can include as a suspending agent a cellulosic suspending agent. Typical viscosities of the suspensions are less than or equal to about 150 centipoise (cps) at ambient conditions.

A pharmaceutical composition as described above may be formulated to have a specific gravity of more than 1 to about 1.5 under ambient conditions. In addition, such formulations may additionally include one or more opacity imparting agents and one or more surfactants such as a non-ionic surfactant, e.g., polysorbate 80.

A pharmaceutical composition as described above may be one in which the suspending agents useful in the present compositions are one or more of methylcellulose, hydroxypropyl methylcellulose (HPMC), sodium carboxypropylmethylcellulose (CPMC), or sodium carboxymethylcellulose and microcrystalline cellulose. As an example, a pharmaceutical composition of the present invention can comprise an opacity imparting agent, a sweetener, and an antioxidant, in which the suspending agent is microcrystalline cellulose and carboxymethylcellulose, or salts thereof. Alternatively, the suspending agent may be microcrystalline cellulose and carboxymethylcellulose sodium. For example, the suspending agents can be (1) microcrystalline cellulose for which the diameter of 60% of the particles of microcrystalline cellulose (its $D_{60}$) is less than 0.2 μm and (2) carboxymethylcellulose sodium.

A pharmaceutical composition as described above may be one in which the suspending agents can be Avicel© RC-591 microcrystalline cellulose and carboxymethylcellulose sodium.

An example of a pharmaceutical composition of the present invention is one which comprises an opacity imparting agent that is mannitol.

A pharmaceutical composition as described above may be one in which the taste-masking agent is a sweetener. The sweetener may include a mono- or a disaccharide and a high intensity sweetener, e.g., stevia, aspartame, sucralose, neotame, acesulfame potassium (Ace-K), saccharin, advantame, or a cyclamate. More specifically, the mono- or disaccharide may be sucrose and the total solids concentration is less than 500 mg/mL. As an example, the concentration of mannitol may be less than 200 mg/mL and the concentration of sucrose may be <300 mg/mL, e.g., the concentration of mannitol may be no more than 100 mg/mL and the concentration of sucrose may be no more than 200 mg/mL, and the total solids concentration may be no more than 350 mg/mL.

In accordance with the above, these tasimelteon-containing compositions may comprise:

(1) a non-ionic surfactant that is polysorbate 80 that is present in a concentration of 0.5 to 5 mg/mL, including a concentration of 1 to 3 mg/mL (or more preferably 1 to 2 mg/mL or most preferably about 1 mg/mL). A pharmaceutical composition as described above may include that in which: tasimelteon present at a concentration of 1 to 6 mg/mL, 2 to 5 mg/mL, 1 mg/mL, or 4 mg/mL.

(2) tasimelteon present at a concentration of 1 to 6 mg/mL or 2 to 5 mg/mL or 1 mg/mL or 4 mg/mL and a suspending agent that is microcrystalline cellulose and sodium carboxymethylcellulose that is present in a concentration of (1) 0 to 30 mg/mL or 10 to 20 mg/mL or 20 mg/mL.

(3) mannitol present as an opacity imparting agent at a concentration (1) no more than 200 mg/mL or (2) less than 200 mg/mL or (3) 50 to 100 mg/mL or (4) 100 mg/mL; sucrose present as a sweetener at a concentration of (1) no more than 300 mg/mL or (2) less than 300 mg/mL or (3) 150 to 250 mg/mL or (4) 200 mg/mL; a high intensity sweetener; polysorbate present as a non-ionic surfactant at a concentration of (1) 1 to 5 mg/mL or (2) 1 to 3 mg/mL or (3) 2 mg/mL; an antioxidant, sodium chloride, and a flavoring agent.

The above compositions may be formulated to exhibit a target pH level. Preferably these compositions are formulated to achieve a targeted pH of 4.0±0.5. In addition, compositions formulated with the above specifications are targeted to exhibit the following release specifications:

(1) Stability: Following storage at each of (1) 5±3° C., (2) 25±2° C. (at 60±5% relative humidity) and (3) 40±2° C. (at 75±5% relative humidity) for successive periods of one, two, or three months, total impurities using high performance liquid chromatography (HPLC) are not more than 1.5 percent by weight, not more than 0.5 percent by weight with respect to known impurities and not more than 0.2 percent by weight with respect to unspecified impurities;

(2) Viscosity: 5 to 30 centapoise (cP or cps), e.g., about 20 cps (at ambient conditions);

(3) Specific Gravity: 1.1 to 1.3 mg/mL;

(4) pH: 4.0 to 5.0;

(5) Particle size distribution: $D_{90}$=100 to 150 μm, $D_{50}$=50 to 70 μm, and $D_{10}$=15 to 40 μm.

(6) Dissolution: greater than or equal to 90% following paddling for 15 minutes (at 50 revolutions per minute (rpm)) in 1N HCl.

The description above relating to "particle size distribution" refers to the percentage of particles within a sample that have a diameter that is greater than, less than, or equal to the stated physical side, e.g., $D_{50}$=50 to 70 μm refers to a sample in which the diameter of 50% of the particles in the same batch have a diameter between 50 and 70 micrometers. As used herein, the particle size distribution refers to measurements undertaken on the tasimelteon particles suspended in the pharmaceutical formulations described herein. Such particle size measurements can be made using laser diffraction techniques, such as laser light scattering detection with a Malvern Mastersizer 2000 or Malvern Mastersizer 3000.

Another aspect of the invention provides a method of treating Smith-Magenis Syndrome (SMS) in a patient in need thereof, the method comprising: determining a body mass of the patient; and in the case that the body mass of the patient is equal to or less than 28 kg, administering to the patient, once daily, a first dose of tasimelteon equal to 0.7 mg/kg; or in the case that the body mass of the patient is greater than 28 kg, administering to the patient, once daily, a second dose of tasimelteon equal to 20 mg.

BRIEF DESCRIPTION OF THE DRAWINGS

These and other features of the invention will be more readily understood from the following detailed description of the various aspects of the invention taken in conjunction with the accompanying drawings that depict various embodiments and aspects of the invention, in which.

Figure 1:
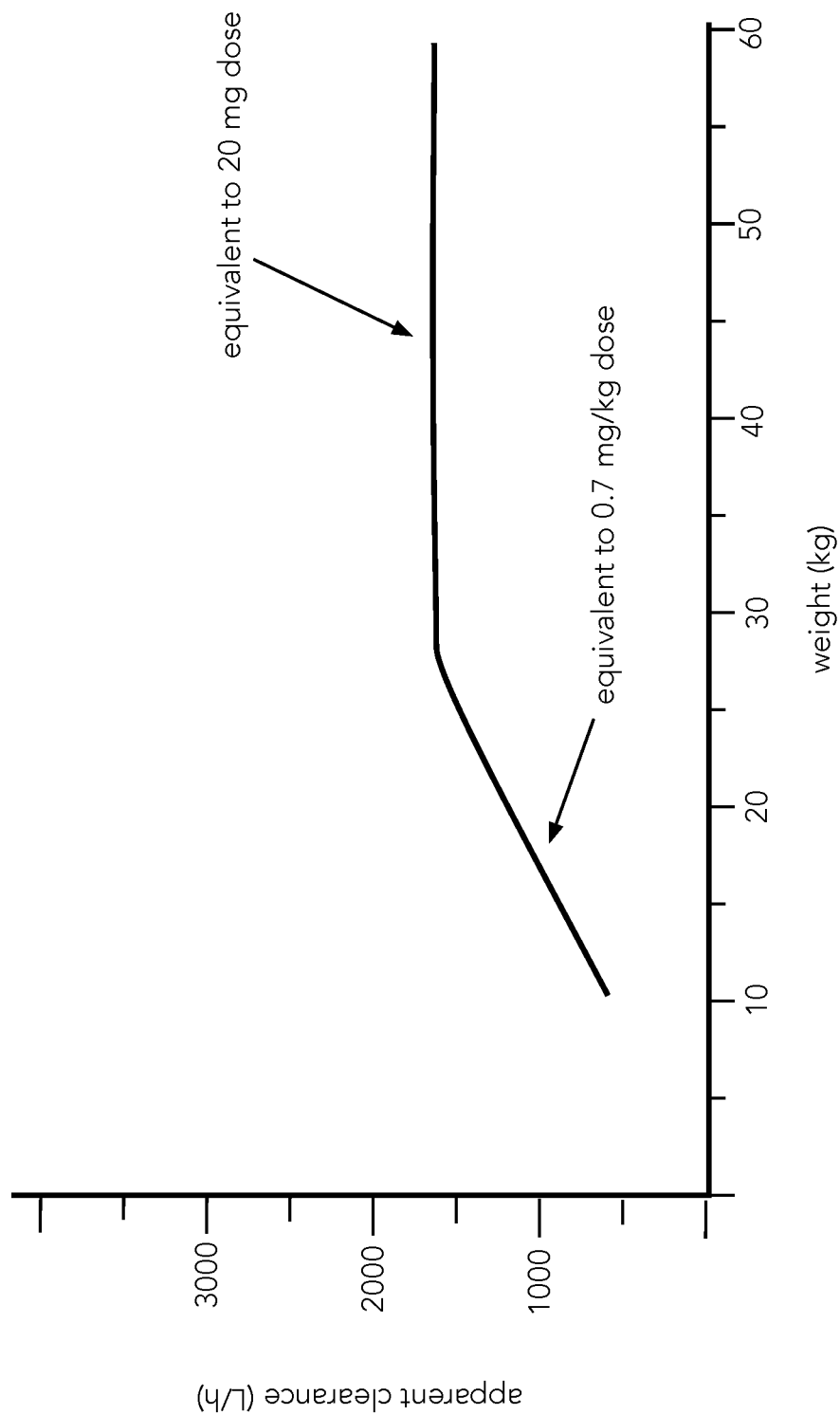
FIG. 1 shows a graph of the effective dose of liquid formulations of tasimelteon as a function of patient body mass.

It is noted that the drawings are not to scale. The drawings are intended to depict only typical aspects of the invention, and therefore should not be viewed as limiting the scope of the invention.

DETAILED DESCRIPTION OF THE INVENTION

Preparing a pharmaceutically elegant liquid suspension of tasimelteon presents a number of difficulties, each of which is addressed in the compositions described below.

Taste

Tasimelteon solubility in water is 1 mg/mL. However, in the presence of formulation excipients, the drug is likely to be essentially insoluble in most suspension formulations. Nonetheless, a trace amount dissolves and imparts a bitter taste to the formulation, which is difficult to mask. Accordingly, the following formulation approaches are considered to improve the taste.

Inclusion of a combination of sucrose, sucralose, and sodium chloride as sweetening/taste masking agents.

Inclusion of Avicel© RC-591, a hydrophilic polymer as suspending agent, which hydrates and swells in the presence of water. A certain amount of water is necessary to properly hydrate and disperse the polymer, plus an additional amount of water is necessary to dissolve ascorbic acid and sodium benzoate. As a result, the amount of water that is available to dissolve sucrose is limited, so 200 mg/mL of sucrose was identified as the maximum amount that could be dissolved.

Since it is not possible to increase the sucrose concentration above 200 mg/mL, sucralose is also included as a sweeting agent at 1 mg/mL, which makes the taste sweeter and thereby helps in better masking the bitter taste.

Additionally, the inclusion of sodium chloride masks the bitter taste and also improves the overall taste at a concentration of 5 mg/mL.

Viscosity

In order to keep tasimelteon drug substance particles in a uniformly suspended state upon shaking, it is necessary to identify a suitable viscosity building agent and its optimum level.

Methylcellulose-A 15C, methylcelluose-A4M and Avicel© RC-591 (microcrystalline cellulose/CMC sodium) are useful as suspending agents. Both grades of methylcellulose produce suspensions that contain polymer particles that are not fully hydrated and their viscosities are on the high side, which adversely affected their dissolution rates.

Avicel© RC-591 at a 6 mg/mL concentration and without homogenization provides desirable physicochemical characteristics, such as rapid dissolution, complete re-dispersion upon gentle shaking of stored suspension bottles, and satisfactory content uniformity.

Chemical Stability

Tasimelteon is susceptible to oxidative degradation, resulting in the formation of three degradation products, thus requiring an antioxidant in the formulation.

Antioxidants such as sodium bisulfite and sodium sulfite were initially considered but have the potential to cause allergic reactions in children.

Ascorbic acid preferentially undergoes oxidation, thereby preventing oxidation of tasimelteon, but also imparts a yellow color to the suspension on storage, especially when stored at 40° C./75% RH for >3 months, which is the accelerated storage condition for products stored at room temperature (6 months of satisfactory stability is necessary at 40° C./75% RH in order to justify long-term storage at room temperature/25° C./60% RH). Because of the color change from white/off-white to yellow after 3 months storage at 40° C./75% RH, it is necessary to store the suspension at 5° C., for which the accelerated storage condition is 25° C./60% RH and up to 6 months of satisfactory stability data at this storage condition are available (i.e., color change is from white/off-white to slightly yellow).

Dissolution

The initial dissolution rate of prototype suspension formulations was rapid (i.e., similar to HETLIOZ© capsule formulations), but dissolution became slower on storage for stability samples.

Polysorbate 80 was evaluated as a surfactant/dissolution enhancer and found to improve the initial dissolution profile, but upon storage, several prototype formulations containing polysorbate 80 exhibited slower dissolution.

Only one prototype formulation (containing tasimelteon 4 mg/mL; sucrose 200 mg/mL; mannitol 100 mg/mL; Avicel© RC-591 20 mg/mL; cherry flavor 5 mg/mL; ascorbic acid 3 mg/mL; sodium benzoate 3 mg/mL; sucralose 1 mg/mL; and purified water QS to 1 mL) provides satisfactory results with respect to suspension appearance, tasimelteon assay, dissolution, impurities/degradation products, and re-dispersibility. Based on satisfactory stability results, this formulation was selected for use in clinical studies.

Opacity

Since the concentration of tasimelteon in the suspension is only 4 mg/mL, the appearance of the suspension is rather translucent and not quite suspension-like, so mannitol at 100 mg/mL is used as an opacity imparting agent.

Although mannitol solubility is ~200 mg/mL in water, the solubility is likely to be much lower in formulation due to the presence of sucrose, ascorbic acid, sodium benzoate, and Avicel© RC591, which dissolve or hydrate. This limits the solubility of mannitol in the formulation, which remains as undissolved particles and imparts opacity to the suspension. It is likely that a small amount of mannitol dissolves in the suspension formulation and thereby adds to the overall sweetness.

Manufacturing Process

Because the formulation contains several ingredients that are either dissolved or dispersed in purified water batch quantity, separate portions of formulation ingredients are prepared (i.e., sucrose was dissolved in hot water (portion 1); tasimelteon, sodium benzoate, ascorbic acid, sucralose, polysorbate 80 and mannitol were dissolved/dispersed and homogenized (portion 2); and Avicel© RC-591 was dispersed in water by simply stirring it without homogenization (portion 3)). The three portions are then mixed to achieve a final uniform suspension.

The Avicel© RC-591 polymer dispersion is prepared by simply stirring the polymer in a portion of the batch water quantity without homogenization. When the polymer dispersion is homogenized, it becomes too viscous, which adversely affects the dissolution rate.

Because of tasimelteon's low melting point (70° C.), it is necessary to maintain the temperature of the suspension in the 50-55° C. range to prevent the drug from melting.

The preparation of liquid pharmaceutical formulations of tasimelteon for use in oral administration can require undesirably large amounts of solvent in order to assure that the active ingredient remains in a homogenous, dissolved state, particularly in the situation where the active ingredient in the formulation has limited aqueous solubility. To address the possibility that unacceptable levels of solvent would be required, the present invention provides a pharmaceutical composition comprising tasimelteon that is formulated as an aqueous liquid suspension that allows one or more unit doses of tasimelteon to be confined an optimal volume (e.g., 0.35 mL to 10 mL of liquid suspension). Most specifically, one embodiment of the present invention allows for a single unit dose to contain an amount of tasimelteon that is effective to treat the individual to whom the medicine is being administered.

Such a suspension is prepared by mixing the tasimelteon with a suspending agent in water. Suspensions are prepared that can be homogeneous, i.e., the tasimelteon is uniformly dispersed, and that can be highly stable. These liquid suspensions of tasimelteon employ tasimelteon that is finely divided and is able to disperse within the suspension. Further, the suspended tasimelteon is substantially undissolved (e.g., at least greater than 50%, or 75%, or 90% undissolved) in the aqueous vehicle of the formulation.

In illustrative embodiments, the tasimelteon is homogeneously or nearly homogeneously dispersed upon shaking or stirring of the pharmaceutical composition. The pharmaceutical composition has a viscosity sufficiently low such that it can be ported for administration orally by spoon, cup, syringe, straw, pharmaceutical dropper, or the like and easily swallowed, including by individuals who have difficulty swallowing a pill or capsule, e.g., some pediatric, elderly, or disabled patients.

In illustrative embodiments, as noted above, the concentration of tasimelteon in the liquid suspensions of the invention is one to six mg/mL. Such embodiments include concentrations that are two to five mg/mL, or about 4 mg/mL (e.g., 3.5 to 4.5 mg/mL), or about 1 mg/mL (e.g., 0.5 to 1.5 mg/mL)

In illustrative embodiments, the liquid vehicle is an aqueous solution comprising a suspending agent and a taste masking agent. Suspending agents are substances added to a suspension to increase viscosity and retard sedimentation. Examples of such agents include cellulosic suspending agents, clays (including, e.g., bentonite and silicates), polysaccharide gums (including xanthan gum, acacia or gum arabic, and tragacanth), other polysaccharides (including agar and carrageenan), synthetic polymers (including carbomer, polyvinylpyrrolidone or PVP, and PVP copolymers such as PVP-vinyl acetate or PVP-VA), and gelatin. Suspending agents in the pharmaceutical compositions are generally effective when present in a concentration range of 1 to 5%.

Cellulosic suspending agents can impart improved characteristics to the pharmaceutical composition relative to other types of suspending agents. These include better stability, reduced sedimentation or better homogeneity. Examples of cellulosic suspending agents are methylcellulose, hydroxypropyl methylcellulose (HPMC), sodium carboxypropylmethylcellulose (CPMC), hydroxyethylcellulose, carboxymethylcellulose, sodium carboxymethylcellulose, and powdered cellulose. Pharmaceutical compositions with particularly advantageous properties may be obtained using Methylcellulose A15C hydroxypropylmethyl cellulose and also with Avicel© RC-591 microcrystalline cellulose+sodium carboxymethylcellulose.

In one illustrative embodiment, the suspending agent comprises compact powder particles comprising microcrystals of microcrystalline cellulose (MCC) and sodium carboxymethylcellulose (CMC), e.g., the product marketed as Avicel© RC-591 MCC+sodium CMC (FMC Corporation, Philadelphia, Pa.), which comprises particles of microcrystals having a particle size $D_{60}$<0.2 μm, wherein the particles are sufficiently compact such that a particle that is 30 μm in diameter contains approximately 600 million MCC+CMC microcrystals that are about 0.1 μm in diameter. Other MCC+CMC suspending agents include a product marketed as VivaPur© MCG MCC+sodium CMC (JRS Pharma, Rosenberg, Germany).

Taste-masking agents include sweeteners such as saccharides, polyols such as mannitol and sorbitol, and synthetic sweeteners, e.g., saccharin and aspartame. Flavoring agents or flavorants (e.g., cherry flavoring) can also be added to mask the taste of the tasimelteon and to make the suspension more palatable especially to children.

Other excipients in the aqueous solution can include opacity imparting agents, coloring agents, surfactants (particularly nonionic surfactants that serve as wetting agents), sweeteners, antioxidants, and preservatives. These and other types of agents that optionally contribute to the stability and homogeneity of the tasimelteon in the pharmaceutical composition, and of the suspension more generally, and optionally contribute to the acceptability of the taste and appearance of the suspension, e.g., flavoring and coloring agents.

High intensity sweeteners are compounds that are severalfold sweeter than sucrose and include, e.g., stevia, aspartame, sucralose, neotame, acesulfame potassium (Ace-K), saccharin, and advantame.

Opacity imparting agents, also known as opacifying agents or opacifiers, include pharmaceutically acceptable insoluble (or poorly soluble) particulate solids that reduce translucence and thereby provide a suspension-like appearance.

Optionally agents are included on the formulation to adjust its pH, e.g., acids, bases, or buffers, including sodium hydroxide, phosphoric acid, or citric acid.

While different categories of agents are identified above by the function they perform in the formulation, various excipients may serve more than one function in the pharmaceutical composition. In addition, the pharmaceutical compositions disclosed herein need not be limited to the specific particle sizes disclosed in the specification.

The tasimelteon used as the active ingredient in the pharmaceutical compositions is prepared, for example, using the same chemistry and manufacturing methods that are known for the preparation of the tasimelteon active ingredient used to prepare solid oral dosage forms, e.g., capsules. See, e.g., US Published Application 20090105333 and PCT Published Application WO2015/123389. Acceptable particle sizes include those as described in these publications, e.g., $D_{50}$ is less than 100 μm, e.g., $D_{50}$ is 20 to 40 μm or 30 to 50 μm. Other illustrative particle size specifications for the tasimelteon active ingredient include, among others:

$D_{10} \leq 30$ μm
$D_{50} \leq 100$ μm
$D_{90} \leq 200$ μm
or
$D_{10} \leq 15$ μm
$D_{50} \leq 45$ μm
$D_{90} \leq 105$ μm.

The particle size measurements described above can be made, e.g., using laser diffraction such as laser light scattering detection with a Malvern Mastercizer.

In an illustrative particle size analysis using such device, a dispersion is prepared by mixing 10 mg polysorbate 80 and 1 g tasimelteon in 1 L of distilled water and then filtered with a 0.2 μm filter. The sampler accessory (Hydro 2000S(A) module) is filled with dispersant to obtain background measurement. Then, about 80-90 mg of sample dispersed in about 15 mL dispersant is slowly added to the sampler accessory until obscuration of about 15% (e.g., 10% to 20%) is obtained. The sample is recirculated at about 2000 rpm for about 5 seconds before measurements are started. Two sample runs are performed and average results are calculated to obtain Do, $D_{50}$, and/or $D_{10}$ values.

To prepare suspensions disclosed herein, all formulation ingredients, except for tasimelteon and other poorly water-soluble ingredients (e.g., ascorbic acid or sodium benzoate) can be dissolved in purified water, optionally previously sparged with nitrogen for 30 minutes. Tasimelteon and other poorly water-soluble ingredients, e.g., mannitol, can be screened such as through a 40-mesh screen to prepare one or more dispersion phases, and then dispersed in the solution of the other formulation ingredients. The dispersion phases comprising tasimelteon are preferably maintained well below the tasimelteon melting point (71° C.), e.g., <35° C. The final aqueous suspension can be filled, for example, into 50 mL or 100 mL amber polyethylene terephthalate (PET) bottles and optionally purged with nitrogen prior to closing the bottles.

An aqueous suspension of tasimelteon comprising a cellulosic suspending agent (methylcellulose A15C), an opacity imparting agent, a thickening/sweetening agent, a high intensity sweetener, a flavoring agent, an antioxidant, and a preservative, such as is described below, can have an improved viscosity and sedimentation profile than one employing crospovidone+povidone (crospovidone XL-10+povidone K30), a thickening agent/sweetener, a high intensity sweetener, a flavoring agent, an antioxidant and a preservative. Viscosity measurements can be performed, e.g., using a Brookfield viscometer DV-III Ultra at 2 hours and 24 hours after each aqueous suspension is prepared. An illustrative pharmaceutical composition comprising PVP and PVP/VA as suspending agents is shown in Table 1.

TABLE 1

Aqueous Suspension-PVP Suspending Agent

| Ingredient | Function | Quantity (mg/mL) |
|---|---|---|
| Tasimelteon | Active ingredient | 4.0 |
| Ascorbic acid | Antioxidant | 3.0 |
| Sorbitol solution 70/02 B | Thickening agent/sweetener | 400.0 |
| Crospovidone XL-10 | Suspending agent | 6.0 |
| Povidone K30 | Suspending agent | 30.0 |
| Sodium benzoate | Preservative | 3.0 |
| Sucralose | Sweetener | 2.0 |
| Flavor | Flavoring agent | 5.0 |
| Purified water | Solvent | QS |

The composition of Table 1 demonstrates acceptable stability. Compositions comprising cellulosic suspending agents have improved properties such as increased viscosity and reduced sedimentation. Illustrative compositions are shown in Table 2.

TABLE 2

Cellulosic Suspending Agent

| Ingredient | Function | A | B | C | D | E | F | G | H | I | J | K | L |
|---|---|---|---|---|---|---|---|---|---|---|---|---|---|
| Tasimelteon | Active ingredient | 4 | 4 | 4 | 4 | 4 | 4 | 4 | 4 | 4 | 4 | 4 | 4 |
| Methylcellulose A15C | Suspending agent | | | | | | | | | | | 6 | |
| Methylcellulose A4M | Suspending agent | | | | | | | | | | | | 7.5 |
| Microcrystalline cellulose/CMC sodium RC-591 | Suspending agent | 20 | 30 | 30 | 30 | | 30 | 10 | 20 | 20 | 20 | 20 | |
| Mannitol | Opacity imparting agent | 100 | 300 | 300 | 300 | | 300 | 100 | 200 | 200 | 200 | 220 | 200 |
| Sorbitol solution 70/02 B | Thickening agent/sweetener | | 100 | | | | | | | | | 100 | |
| Ascorbic acid | Antioxidant | 3 | 2 | 2 | 2 | 2 | 2 | 2 | 2 | 2 | 2 | 3 | 2 |
| Sodium benzoate | Preservative | 3 | 3 | 3 | 3 | 3 | 3 | 3 | 3 | 3 | 3 | 3 | 3 |
| Sucrose | Sweetener | 200 | | 300 | 300 | | 300 | 300 | 300 | 300 | 300 | | 300 |
| Sucralose | Sweetener | 1 | 1 | | 0.25 | | | | | | | 1 | |
| Sodium chloride | Tonicity Agent | 5 | | | | 5 | 5 | 5 | 5 | 5 | 5 | | 5 |
| Polysorbate 80 | Surfactant | 2 | | | | | | | 1 | 3 | 3 | | 3 |
| Flavor art cherry powder F-10052 | Flavoring agent | 5 | 5 | 5 | 5 | 5 | 5 | 5 | 5 | 5 | 5 | 5 | 5 |
| Purified water | Solvent/Vehicle | QS | QS | QS | QS | QS | QS | QS | QS | QS | QS | QS | QS |

Compositions comprising sucrose in place of sorbitol and comprising sodium chloride can have improved taste and reduced bitterness (or burning sensation).

The microcrystalline cellulose+carboxymethylcellulose (CMC) sodium suspending agent, 10 to 30 mg/mL, particularly 20 mg/mL, can provide improved stability and physical appearance (homogeneity).

Mannitol is useful as an opacity imparting agent, e.g., when used at 100 to 300 mg/mL. The range of 100 to 200 mg/mL, particularly 100 mg/mL, provided enhanced dissolution and viscosity, particularly when combined with a reduction in sucrose from 300 to 200 mg/mL.

Dissolution of tasimelteon is determined in accordance with the US Pharmacopeia (USP<711>), e.g., Apparatus: Apparatus 2 (paddle)
Vessel Size/Type: 1000 mL, clear glass, round bottom
Rotation Speed: 50 rpm
Test Temp: 37±0.5° C.
Dissolution Media: 0.1 N HCl
Pull Volume: 5 mL
Replacement: No
Sinker: No
Cannula: Stainless steel
Filter: Whatman GF/F 0.7 µm pore size, syringe filer
Volume Discard: 2 mL
Dissolution at 10 to 15 minutes is generally at least 50%, e.g., at least 70%, e.g., at least 90%.

Short-term stability studies can be undertaken under storage conditions at (1) 5±3° C., (2) 25±2° C. (at 60±5% relative humidity), and 40±2° C. (at 75±5% relative humidity) for one to three months. Under such conditions, total impurities as determined by HPLC for pharmaceutically acceptable compositions are, for example, not more than 2.0 percent by weight or not more than 0.5 percent by weight with respect to known impurities, and not more than 0.2 percent by weight with respect to unspecified impurities.

Viscosity measurements can be performed, e.g., using a Brookfield viscometer DV-III Ultra at 2 hours and 24 hours after each aqueous suspension is prepared. Viscosity values can in general be up to about 150 cps at ambient conditions (i.e., 18° C. to −24° C., e.g., −20° C., and about 1 atmosphere), but viscosity levels of certain embodiments are 5 to 100 cps, e.g., 5 to 50 cps or 5 to 20 cps.

The specific gravity (relative density) of the suspension is typically greater than 1 and up to about 1.5 mg/mL at ambient conditions, e.g., 1.1 to 1.3 mg/mL.

A satisfactory pH is generally in the range of pH 3 to 7, e.g., pH 4 to 5 or pH 4.0 to 4.5.

With respect to particle size, improved results can be obtained with particle sizes that include $D_{90} \leq 150$ µm, e.g., 100 to 150 µm; $D_{50}$ 80 µm, e.g., 50 to 70 µm; $D_{10} \leq 50$ µm, e.g., 15 to 40 µm.

Thus, in one embodiment, the formulation of the invention meets at least the following specifications on release for commercial distribution:

Stability: Following storage at (1) 5±3° C., (2) 25±2° C. (at 60±5% relative humidity), and (3) 40±2° C. (at 75±5% relative humidity) for one, two, or three months, total impurities (HPLC) are not more than 1.5 percent by weight, not more than 0.5 percent by weight with respect to known impurities and not more than 0.2 percent by weight with respect to unspecified impurities;

Viscosity: 5 to 30 cps, e.g., 20 cps (ambient conditions);
Specific Gravity: 1.1 to 1.3 mg/mL;
pH: 4.0 to 5.0;

Particle size: $D_{90}$=100 to 150 μm, $D_{50}$=50 to 70 μm, and $D_{10}$=15 to 40 μm.

Dissolution: ≥90% following paddling for 15 minutes at 50 rpm in 1N HCl.

As described above, alternative suspending agents includes polysaccharide gums. For example, promising results have been obtained with xanthan gum, e.g., 1 to 25 mg/mL, preferably 1 to 5 mg/mL. Illustrative compositions comprising a polysaccharide gum as the suspending agent and titanium dioxide as an opacity imparting agent are provided in Table 3.

TABLE 3

Polysaccharide Gum Suspending Agent

| Ingredient | Formulation (mg/mL) | | |
|---|---|---|---|
| | M | N | O |
| Tasimelteon | 4 | 4 | 4 |
| Xanthan Gum (Xantural 75) | 25 | 2 | 2 |
| Titanium Dioxide | 1 | 1 | 1 |
| Ascorbic Acid | 2 | 2 | 2 |
| Sodium Benzoate | 3 | 3 | 3 |
| Sucrose | 200 | 200 | 200 |
| Sodium Chloride | 5 | 5 | 5 |
| Polysorbate 80 | 2 | 2 | 2.5 |
| Cherry Flavor | 5 | 5 | 5 |
| Sucralose | 1 | 1 | 1 |
| Purified Water | QS | QS | QS |

Dosing and Administration

Smith-Magenis Syndrome (SMS) is a rare, clinically recognizable syndrome characterized by a distinct pattern of minor craniofacial and skeletal anomalies, expressive speech/language delays, psychomotor and growth retardation, and a striking neurobehavioral phenotype (stereotypies, self-injurious, and aggressive behaviors). SMS and its treatment with tasimelteon are described, for example, in PCT Publication No. WO 2016/036619, which is incorporated herein by reference.

One common symptom of SMS is a chronically disrupted sleep pattern, which is found at all ages. In a study to determine the efficacy of tasimelteon in the treatment of disorders, including SMS, oral (20 mg capsule or 4 mg/mL suspension) and intravenous (0.4 mg/mL) formulations were administered once per day before bedtime to pediatric patients 3-17 years old.

Treatment efficacy was assessed by improvements in nighttime sleep (i.e., reduced nighttime activity interrupting the sleep period, improved sleep efficiency, reduced variability in sleep onset, reduced variability in morning awakenings, and/or improved sleep quality), reduced daytime sleepiness, reduced behavioral problems (i.e., reduced aggressive behavior, reduced temper tantrums, reduced hyperactivity, and/or reduced attention deficits).

Surprisingly, a consistently effective dose of tasimelteon was found to be proportional to body mass (0.7 mg/kg) for those patients having a body mass of 28 kg or less, but 20 mg for those patients having a body mass greater than 28 kg. That is, apparent clearance in children with a body mass greater than 28 kg was constant and similar to that of adults. This result was unexpected but consistent and independent of other variables, including patient age and sex.

FIG. 1 shows a graph of the effective dose of tasimelteon (measured as apparent clearance, the inverse of which is systemic exposure) as a function of patient body mass. As can be seen, the effective dose is proportional to body mass (0.7 mg/kg) up to a body mass of 28 kg, after which, the corresponding effective dose is a constant 20 mg.

Such dosing is applicable to any of the liquid formulations containing tasimelteon described herein or any other formulation suitable for administration according to such a dosing regimen. For example, such liquid formulations may be employed to administer a daily dose of 0.7 mg/kg to a patient having a body mass of 28 kg or less as well as to administer a daily dose of 20 mg to a patient having a body mass greater than 28 kg. Alternatively, a liquid formulation according to the invention may be employed to administer a daily dose of 0.7 mg/kg to a patient having a body mass of 28 kg or less and another tasimelteon formulation, such as a capsule, tablet, or intravenous formulation, used to administer a daily dose of 20 mg to a patient having a body mass greater than 28 kg.

Figure 2:
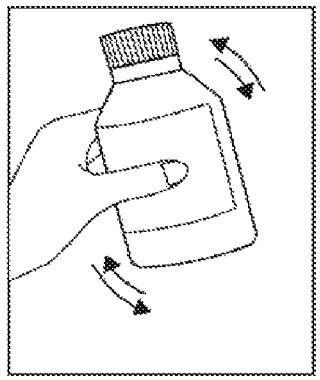
FIG. 2 shows graphical representations of various steps in the administration of liquid formulations of tasimelteon according to embodiments of the invention.
Figure 2:
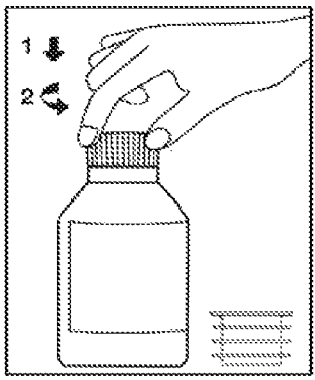
Figure 2:
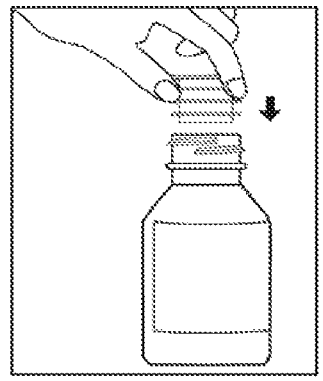
Figure 2:
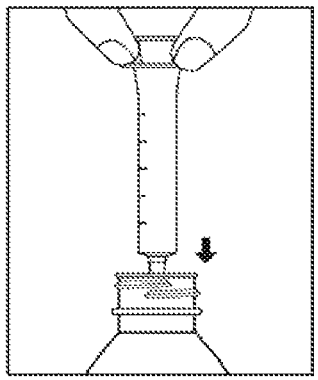
Figure 2:
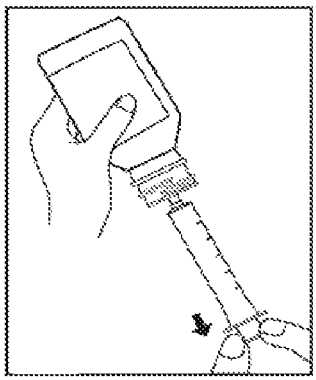
Figure 2:
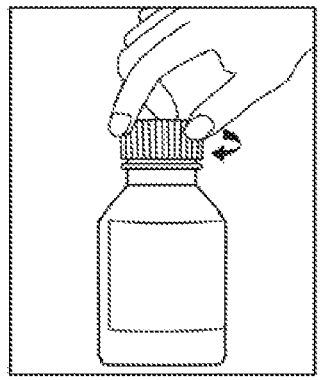

FIG. 2 shows a series of graphical representations of various steps of a method suitable for the administration of liquid formulations of tasimelteon according to embodiments of the invention. In panel A, a bottle containing a liquid formulation of tasimelteon, such as those formulations described above, is shaken well for at least 15 seconds (e.g., at least about 30 seconds) before use. This step has been shown to be important in ensuring that components of the formulations, including tasimelteon, are sufficiently mixed to achieve the benefits noted above and to allow for consistent, accurate dosing of tasimelteon.

In panels B and C, respectively, the bottle is uncapped after shaking and a bottle adapter is inserted into the neck of the bottle. As one skilled in the art will recognize, use of a bottle adapter is neither critical nor necessary, but is often helpful in the use of a syringe, described below, in administering liquid formulations of all types, including liquid formulations of tasimelteon according to embodiments of the invention.

In panels D and E, respectively, a syringe is inserted into an opening of the bottle adapter and both the bottle and inserted syringe are inverted in order to allow drawing of a prescribed amount of the liquid formulation into the syringe. The drawn dose may then be administered to a patient (not shown) orally, directly from the syringe or otherwise. In panel F, the cap is replaced on the bottle until next used again.

Further illustrative embodiments of the invention are described in the following sets of claims. Like the formulations and methods illustrated above, these are intended to be illustrative and not limiting of the invention, which encompasses modifications and variations of such illustrative embodiments.

The invention claimed is:

1. A method of treating Smith-Magenis Syndrome (SMS) in a patient in need thereof, the method comprising:
   determining a body mass of the patient; and
   in the case that the body mass of the patient is equal to or less than 28 kg, administering to the patient, once daily, a first dose of tasimelteon equal to 0.7 mg/kg in a liquid formulation, wherein the method includes shaking the liquid formulation for at least 15 seconds before administering to the patient; or
   in the case that the body mass of the patient is greater than 28 kg, administering to the patient, once daily, a second dose of tasimelteon equal to 20 mg.

2. The method of claim 1, wherein the liquid formulation comprises:
   a homogeneous aqueous suspension of tasimelteon;
   a suspending agent;
   a taste-masking agent;
   an opacity-imparting agent; and
   a surfactant,
   wherein the composition has a viscosity less than or equal to 150 cps and a specific gravity of greater than 1-1.5 under ambient conditions.

3. The method of claim 2, wherein the suspending agent includes at least one cellulosic suspending agent selected from a group consisting of: methylcellulose, hydroxypropyl methylcellulose (HPMC), sodium carboxypropylmethylcellulose (CPMC), carboxymethylcellulose sodium, and microcrystalline cellulose.

4. The method of claim 3, wherein the at least one cellulosic suspending agent includes microcrystalline cellulose and carboxymethylcellulose sodium.

5. The method of claim 2, wherein tasimelteon is present in the liquid formulation at a concentration of:
   1 to 6 mg/mL; or
   2 to 5 mg/mL; or
   1 mg/mL; or
   4 mg/mL; and
   the suspending agent is microcrystalline cellulose and sodium carboxymethylcellulose and is present in a concentration of:
   10 to 30 mg/mL; or
   10 to 20 mg/mL; or
   20 mg/mL.

6. The method of claim 2, wherein the liquid formulation comprises:
   mannitol as the opacity-imparting agent at a concentration of:
   no more than 200 mg/mL; or
   less than 200 mg/mL; or
   50 to 100 mg/mL; or
   100 mg/mL;
   sucrose as the taste-masking agent at a concentration of:
   no more than 300 mg/mL; or
   less than 300 mg/mL; or
   150 to 250 mg/mL; or
   200 mg/mL; and
   polysorbate 80 as the surfactant at a concentration of:
   1 to 5 mg/mL; or
   1 to 3 mg/mL; or
   2 mg/mL.

7. A method of treating Smith-Magenis Syndrome (SMS) in a patient in need thereof, the method comprising:
   determining a body mass of the patient; and
   in the case that the body mass of the patient is equal to or less than 28 kg, administering to the patient, once daily, a first dose of tasimelteon equal to 0.7 mg/kg in a liquid formulation, wherein the method includes shaking the liquid formulation for at least 30 seconds before administering to the patient; or
   in the case that the body mass of the patient is greater than 28 kg, administering to the patient, once daily, a second dose of tasimelteon equal to 20 mg.

8. The method of claim 7, wherein the liquid formulation comprises:
   a homogeneous aqueous suspension of tasimelteon;
   a suspending agent;
   a taste-masking agent;
   an opacity-imparting agent; and
   a surfactant,
   wherein the composition has a viscosity less than or equal to 150 cps and a specific gravity of greater than 1-1.5 under ambient conditions.

9. The method of claim 8, wherein the suspending agent includes at least one cellulosic suspending agent selected from a group consisting of: methylcellulose, hydroxypropyl methylcellulose (HPMC), sodium carboxypropylmethylcellulose (CPMC), carboxymethylcellulose sodium, and microcrystalline cellulose.

10. The method of claim 9, wherein the at least one cellulosic suspending agent includes microcrystalline cellulose and carboxymethylcellulose sodium.

11. The method of claim 8, wherein tasimelteon is present in the liquid formulation at a concentration of:
    1 to 6 mg/mL; or
    2 to 5 mg/mL; or
    1 mg/mL; or
    4 mg/mL; and
    the suspending agent is microcrystalline cellulose and sodium carboxymethylcellulose and is present in a concentration of:
    10 to 30 mg/mL; or
    10 to 20 mg/mL; or
    20 mg/mL.

12. The method of claim 8, wherein the liquid formulation comprises:
    mannitol as the opacity-imparting agent at a concentration of:
    no more than 200 mg/mL; or
    less than 200 mg/mL; or
    50 to 100 mg/mL; or
    100 mg/mL;
    sucrose as the taste-masking agent at a concentration of:
    no more than 300 mg/mL; or
    less than 300 mg/mL; or
    150 to 250 mg/mL; or
    200 mg/mL; and
    polysorbate 80 as the surfactant at a concentration of:
    1 to 5 mg/mL; or
    1 to 3 mg/mL; or
    2 mg/mL.

13. The method of claim 12, wherein the liquid formulation further comprises:
    a high-intensity sweetener;
    an antioxidant;
    sodium chloride; and
    a flavoring agent.

14. The method of claim 6, wherein the liquid formulation further comprises:
    a high-intensity sweetener;
    an antioxidant;
    sodium chloride; and
    a flavoring agent.

* * * * *